(12) United States Patent
Fujii et al.

(10) Patent No.: US 8,708,915 B2
(45) Date of Patent: Apr. 29, 2014

(54) ULTRASONIC PROBE

(75) Inventors: Kiyoshi Fujii, Kanagawa (JP); Akira Shimasaki, Kanagawa (JP); Eiichi Ookawa, Kanagawa (JP); Masahiro Shinkai, Tokyo (JP)

(73) Assignee: Panasonic Corporation, Osaka (JP)

( * ) Notice: Subject to any disclaimer, the term of this patent is extended or adjusted under 35 U.S.C. 154(b) by 189 days.

(21) Appl. No.: 13/123,381

(22) PCT Filed: Dec. 2, 2009

(86) PCT No.: PCT/JP2009/006522
§ 371 (c)(1),
(2), (4) Date: Apr. 8, 2011

(87) PCT Pub. No.: WO2010/064415
PCT Pub. Date: Jun. 10, 2010

(65) Prior Publication Data
US 2011/0201937 A1 Aug. 18, 2011

(30) Foreign Application Priority Data
Dec. 2, 2008 (JP) .................................. 2008-307271

(51) Int. Cl.
*A61B 8/00* (2006.01)
(52) U.S. Cl.
USPC ............ 600/459; 600/407; 600/437; 600/446
(58) Field of Classification Search
USPC .......................... 600/407, 437, 446–447, 459
See application file for complete search history.

(56) References Cited

U.S. PATENT DOCUMENTS

| 5,152,294 A | 10/1992 | Mochizuki et al. |
| 5,460,179 A * | 10/1995 | Okunuki et al. ............... 600/444 |
| 2004/0133105 A1 * | 7/2004 | Ostrovsky et al. ............ 600/437 |
| 2007/0044336 A1 * | 3/2007 | IIkubo et al. .................... 33/503 |

FOREIGN PATENT DOCUMENTS

| JP | 59-111110 U | 7/1984 |
| JP | 59-190208 U | 12/1984 |
| JP | 61-13942 A | 1/1986 |
| JP | 61-234697 A | 10/1986 |

(Continued)

OTHER PUBLICATIONS

International Search Report for PCT/JP2009/006522 dated Feb. 16, 2010.

(Continued)

*Primary Examiner* — Tse Chen
*Assistant Examiner* — Joel F Brutus
(74) *Attorney, Agent, or Firm* — Pearne & Gordon LLP

(57) ABSTRACT

The invention provides an ultrasonic probe having a frame to constitute a part of a cubicle, a motor fixed on the frame, a first arm with one end fixed on a rotating shaft of the motor, and a second arm with one end rotatably coupled with the other end of the first arm via a coupling shaft and with the other end having an ultrasonic element mounted thereon. The second arm has a lengthwise long groove and is slidably engaged with the fixed shaft of the frame in the direction of length. The length from an end of the second arm where the ultrasonic element is mounted on the coupling shaft is designed to be longer than the length from the rotating shaft to the coupling shaft, and further, to be longer than the length from the rotating shaft to the fixed shaft.

35 Claims, 13 Drawing Sheets

(56) References Cited

FOREIGN PATENT DOCUMENTS

| | | | |
|---|---|---|---|
| P | 62-137007 | U | 8/1987 |
| JP | 03-184532 | A | 8/1991 |
| JP | 3-184532 | A | 8/1991 |
| JP | 4-282136 | A | 10/1992 |
| JP | 10-201762 | A | 8/1998 |
| WO | 2008/010558 | A1 | 1/2008 |

OTHER PUBLICATIONS

Chinese Office Action for Application 20098014803-8 Dated Dec. 6, 2012.

European Search Report for Application No. 09830185 dated Oct. 23, 2013.

* cited by examiner

000# ULTRASONIC PROBE

TECHNICAL FIELD

The present invention relates to an ultrasonic probe, which is used in an ultrasonic diagnostic apparatus and has a primary aim to take three-dimensional tomography of the regions such as mammary gland, thyroid gland, carotid arteries, superficial blood vessels, superficial region of body surface, etc. (hereinafter, referred as "superficial tissues"). In particular, the invention relates to an ultrasonic probe, which scans over body surface by mechanically swinging and oscillating the ultrasonic element.

BACKGROUND ART

For the purpose of obtaining three-dimensional ultrasonic diagnostic image of human superficial tissues as described above conveniently and within short time, it is necessary to have a wide visual field by an array type element near the surface of human body and mechanical scanning along the shape of human body surface in a direction perpendicularly crossing the scanning direction of the array type element. However, a hand-carried ultrasonic probe has such advantages that three-dimensional images of all types of superficial tissues are obtained by a single three-dimensional ultrasonic probe, and troublesome procedure during diagnosis to exchange the probe can be eliminated and there is no need to use a plurality of three-dimensional ultrasonic probes, and it is very advantageous from the viewpoint of cost. On the other hand, in the ultrasonic probe to obtain three-dimensional tomograms of the regions such as carotid arteries, thyroid gland, etc., the size of the probe must be made as small as possible because of the site of human body to be diagnosed under chin. Thus, there are demands, which contradict against each other, i.e. the necessity to have wider three-dimensional diagnostic region and the realization of the demands to have smaller type of three-dimensional ultrasonic probe. Because it is a hand-carried ultrasonic probe, the probe must be in small size and light in weight.

The present invention provides the means to solve the problems, i.e. the problem of small size and lightweight design to have wider diagnostic region and the probe in smaller size, and the problem to ensure adherence to or close contact with the part of human body, which is relatively flat.

As a conventional method to acquire tomograms of superficial human tissues, the Patent Document 1 as given below discloses means for obtaining tomographic image of the entire mamma (breast), which uses an applicator for breast on the ultrasonic probe, and the tomographic image of the entire region of mamma is obtained by rotating the probe itself.

However, the invention disclosed in the Patent-Document 1 describes an apparatus to be exclusively used for the diagnosis of mammary gland by rotating the existing array type ultrasonic probe. Doctors cannot operate it by directly gripping the probe in the same manner as the case of the hand-carried ultrasonic probe. In addition, other diagnostic regions such as carotid arteries, thyroid gland, etc. cannot be diagnosed by a single three-dimensional ultrasonic probe.

The Patent-Document 2 as given below describes the means to obtain tomographic image of the entire mamma by arranging the ultrasonic probe in water tank and by moving the probe in parallel direction. Also, the Patent Document 3 as given below describes means for acquiring ultrasonic image by moving the ultrasonic probe in parallel direction by using belt or the like.

However, similarly to the case of the Patent Document 1, the Patent Document 2 does not describe a hand-carried three-dimensional ultrasonic probe. The apparatus itself is in large scale and troublesome procedures are required in the preparation in advance. Also, diagnosis cannot be conveniently made on other diagnostic regions such as carotid arteries, thyroid gland, etc. Further, by applying the embodiment of the Patent Document 3, a mechanism to move the ultrasonic element in parallel direction by means of a wire 31 can be used to estimate the use of the hand-carried ultrasonic probe as shown in FIG. 20. However, when the array type element 30 is moved in parallel by using wire, timing belt, etc., a pulley 32 must be used to drive the wire 31 or the like on both ends of the element to be moved. Therefore, when the structure of this type is used, as shown in FIG. 21, moving range must be restricted, and this gives restriction on the width of the element 30 or on the diameter of the pulley 32, and wide contact region of human body is required, which is wider than the mechanical moving range, and this cannot be applied in case of the hand-carried three-dimensional ultrasonic probe. In particular, when diagnosis must be made on carotid arteries, thyroid gland, etc., the hand-carried three-dimensional ultrasonic probe has such problems that chin and other region of human body may hinder the application of the hand-carried three-dimensional ultrasonic probe. FIG. 20 and FIG. 21 each represents a case where the ultrasonic element 30 is mounted so that it can be moved in parallel by using a slide bearing 33, and the ultrasonic element is moved in parallel by rotary movement of the motor 34 and by a transmission mechanism using the pulley 32 and the wire 31.

The Patent Document 4 as given below describes the means to use the hand-carried three-dimensional ultrasonic probe by rotating around one end of the array type element in electronic scanning direction as the center.

However, when the means to acquire three-dimensional ultrasonic image is used, in which one end in electronic scanning direction of the array type element is rotated around it as in the case of the invention of the Patent Document 4, rotary momentum of a part away from the center of rotation is increased more compared with the rotation momentum near the center of the mechanical rotation. As a result, the pitch of two-dimensional cross-sectional area, which serves as the original data to build up the three-dimensional tomographic image, is finer in the region nearer to the rotation center, and the pitch is rougher as it goes away from the rotation center. In proportion to the distance from the rotation center, the pitch of the slice cross-section of the two-dimensional cross-sectional surface is turned to be rougher. Thus, when three-dimensional image is built up by using the cross-sectional image data at a position away from the rotation center, resolution will be rougher at the site away from the rotation center. Further, because, in the electronic scanning, the array type element is rotating around the end portion as the center, a mechanism is needed, which has the rotation center axis at a position away from the length of the element of the electron scanning direction of the array type element. When it is necessary to diagnose the site such as carotid arteries, thyroid gland, etc., the human body contacting region, which is larger than the length of the element, touches the region of chin, and it is difficult to have the ultrasonic probe properly at a position as desired.

In the three-dimensional ultrasonic probe as described in the Patent Document 5, description is given on the means, by which the hand-carried three-dimensional ultrasonic probe can be used by obtaining three-directional ultrasonic tomographic image through mechanical swinging of a convex type array element.

However, in the three-dimensional ultrasonic probe as described in the Patent Document 5, the curvature of the tip of the probe, which comes into contact with the aimed site of human body, is determined, depending on the distance from the swinging rotation center of the element to the tip of the array type element because three-dimensional ultrasonic tomographic image can be obtained by mechanically swinging the convex type array element. In case it is necessary to bring the probe into contact with the site of the tissue, which is relatively flat, i.e. in order to have human body to be contacted by two ends through mechanical swinging scanning, it is necessary to have longer distance from the rotation center of mechanical swinging to the tip of the array type element and to increase the curvature of the human body contact region. However, in order to increase the distance from the rotation center of the mechanical swinging to the tip of the array type element, the entire size of the hand-carried three-dimensional ultrasonic probe must be larger, and the increase of the size and the weight of the hand-carried three-dimensional ultrasonic probe causes such problems that the probe is difficult to handle for the purpose of diagnosis.

PRIOR ART DOCUMENT

Patent Document

Patent Document 1: Japanese Patent Application Publication No. 59-190208 (p. 10; FIG. 3 and FIG. 6).
Patent Document 2: Japanese Patent Application Publication No. 59-111110 (pp. 3-4; FIG. 3).
Patent Document 3: Japanese Patent Application Publication No. 61-13942 (p. 2, left lower column to p. 3, left upper column).
Patent Document 4: Japanese Patent Application Publication No. 4-282136 (Paragraphs 0038-0043).
Patent Document 5: Japanese Patent Application Publication No. 3-184532 (p. 3, left lower column to p. 4, left upper column).

SUMMARY OF THE INVENTION

To solve the problems as described above, it is an object of the present invention to provide an ultrasonic probe of hand-carried mechanical scanning type, which is suitable for diagnosis of human superficial tissues at the site such as breast, carotid arteries, thyroid gland, etc.

The invention provides an ultrasonic probe, which comprises a frame to constitute a part of a cubicle, a first arm with one end fixed on a first shaft member, and a second arm with one end rotatably connected to the other end of said first arm via a coupling shaft and provided with an ultrasonic element to mutually convert electric signals and ultrasonic signals on the other end, wherein said second arm has a lengthwise long groove and is slidably engaged with the second shaft member in the direction of its length, the length from an end portion where said ultrasonic element of said second arm is mounted to said coupling shaft is designed to be longer than the length from said first shaft member to the coupling shaft of said first arm, and is designed to be longer than the length from said first shaft member to said second shaft member, a swinging mechanism containing said first arm and said second arm is disposed in a cubicle surrounded by an ultrasonic window and said frame, and an acoustic coupling liquid is sealed so that said ultrasonic element is swung and scanned.

With the arrangement as described above, by fixedly rotating the rotating shaft to the motor on a first shaft member and a second shaft member, a second arm is swung in moving in a direction of the length of the second arm with the second shaft member as fulcrum. By the action of the first arm and the second shaft member, the ultrasonic probe mounted on the tip of the second arm can be swung with a locus with larger curvature.

Also, the present invention provides the ultrasonic probe as described above, wherein a length from said first shaft member to a coupling shaft to couple said second arm is the same as the length from said first shaft member to said second shaft member, and a triangle formed by said first shaft member, by the coupling shaft of said first arm and said second arm, and by said second shaft member make up together an isosceles triangle.

With the arrangement as described above, when the first arm is rotated, the triangle always forms an isosceles triangle. Tilting angle of the second arm where the ultrasonic element is mounted is always at an angle of ½ to the rotation angle of the first shaft member, and rotation angle of the first shaft member and tilting angle of the arm where the ultrasonic element is mounted can be maintained always in a constant relation.

Further, the present invention provides the ultrasonic probe as described above, wherein a length from said first shaft member to the coupling shaft to couple with said second arm is designed to be longer than the length from said first shaft member to the said second shaft member where said second arm is slidably engaged.

With the arrangement as described above, the ultrasonic element fixed at the tip of the second arm can be moved widely at a swinging angle smaller than that of the first arm.

Also, the present invention provides the ultrasonic probe, comprising a frame to constitute a part of a cubicle, a first arm with one end fixed on a first shaft member, and a second arm with one end rotatably connected to the other end of said first arm via a coupling shaft and provided with an ultrasonic element to mutually convert electric signals and ultrasonic signals on the other end, said second arm is designed as slidable on a second shaft member via a slide bearing unit, a swinging mechanism containing said first arm and said second arm is disposed in a cubicle surrounded by an ultrasonic window and said frame, and an acoustic coupling liquid is sealed so that said ultrasonic element is swung and scanned.

With the arrangement as described above, by mounting a slide bearing on the second arm, the second arm can be slid to the second shaft member so that it can move in the length direction. Compared with the arrangement based on the groove and the second shaft member as given above, the shakiness caused by the moving of gap does not occur, and smooth movement of the second arm can be assured.

Further, the present invention provides the ultrasonic probe as described above, wherein said ultrasonic element is rotatably mounted on said second arm, a groove type rail is provided on said frame or on said ultrasonic window so that a guiding shaft disposed on the ultrasonic element is engaged with said groove type rail.

With the arrangement as described above, ultrasonic waves transmitted and received to and from the ultrasonic element can be transmitted and received in a direction perpendicular to the window. Also, by giving elaborate design on the shape of the rail, the angle to transmit and receive the ultrasonic waves to and from human body can be set as desired, and the direction of the ultrasonic waves to and from human body can be set in a direction parallel or in fan-shaped form, depending on the purpose of the diagnosis.

Also, the present invention provides the ultrasonic probe as described above, wherein said ultrasonic element is rotatably mounted on said second arm, a convex type rail is disposed on said frame or on said ultrasonic window, and said convex type rail is squeezed by two or more guiding shafts provided on said ultrasonic element.

Further, the present invention provides the ultrasonic probe as described above, wherein said ultrasonic element is rotatably mounted with respect to said second arm, a groove type rail is provided on said frame or on said ultrasonic window, and a guiding shaft disposed on said ultrasonic element and a second guiding shaft disposed in such manner that said second guiding shaft is repelled to said guiding shaft by force of a spring are engaged on said groove type rail mounted on said frame or said ultrasonic window.

With the arrangement as described above, one guiding shaft is fixed on the element unit having ultrasonic element inside the groove type rail, and the shakiness of the element unit can be reduced by so arranging that the other guiding shaft is repelled by force of a spring and can be pressed on inner wall of the groove of the rail.

Also, the present invention provides the ultrasonic probe as described above, wherein said ultrasonic element is rotatably mounted on said second arm, a convex type rail is disposed on said frame or on said ultrasonic window, and a guiding shaft provided on said ultrasonic element and a second guiding shaft provided to pull each other by force of a spring to said guiding shaft so that said convex type rail disposed on said frame or on said ultrasonic window is squeezed.

With the arrangement as described above, one guiding shaft, which is fixed on the element unit provided with an ultrasonic element, and the other guiding shaft are pulled to each other by force of a spring. As a result, the shakiness of the guiding shaft and the convex type rail can be reduced.

Further, the present invention provides the ultrasonic probe as described above, wherein a bearing or a resin material having low friction resistance is provided on a forward end where said groove type rail or said convex type rail comes into contact with said guiding shaft.

With the arrangement as described above, bearing is disposed at the tip of the guiding shaft or Teflon resin with lower friction resistance can be mounted at the tip of the guiding shaft, and the element unit having ultrasonic element can be rotated smoothly along the shape of the rail.

Also, the present invention provides the ultrasonic probe as described above, wherein an elastic material such as rubber or resin is provided on both or one of said groove type rail or said convex type rail and said guiding shaft on a portion where said groove type rail or said convex type rail and said guiding shaft come into contact with each other.

With the arrangement as described above, by mounting an elastic member such as rubber on a surface where a guiding shaft or a groove type rail or a convex type rail comes into contact, the shakiness caused between the guiding shaft and the groove type rail or the convex type rail can be reduced.

Further, the present invention provides the ultrasonic probe as described above, wherein said ultrasonic element is an electronic scanning type element and is mechanically swung in a direction to perpendicularly cross the electronic scanning by said swinging mechanism.

With the arrangement as described above, the ultrasonic element is an element of electronic scanning type, and electronic scanning can be carried out in the scanning by mechanical swinging in a direction perpendicular to the scanning by mechanical swinging. As a result, it is possible to provide an ultrasonic probe, which can carry out three-dimensional scanning by electronic scanning and mechanical scanning.

By the ultrasonic probe according to the present invention, the ultrasonic element can be mechanically swung with a large swinging curvature by a small type swinging mechanism. This makes it possible to have the hand-carried ultrasonic probe in small and lightweight design, and ultrasonic probe can be realized, which shows better operability during diagnosis. In particular, the invention has such effects that wider visual field can be obtained by a small size and lightweight ultrasonic probe for a relative larger region near body surface, which is required for an ultrasonic probe to perform diagnosis on superficial region of human body.

DESCRIPTION OF EMBODIMENTS

Figure 1:
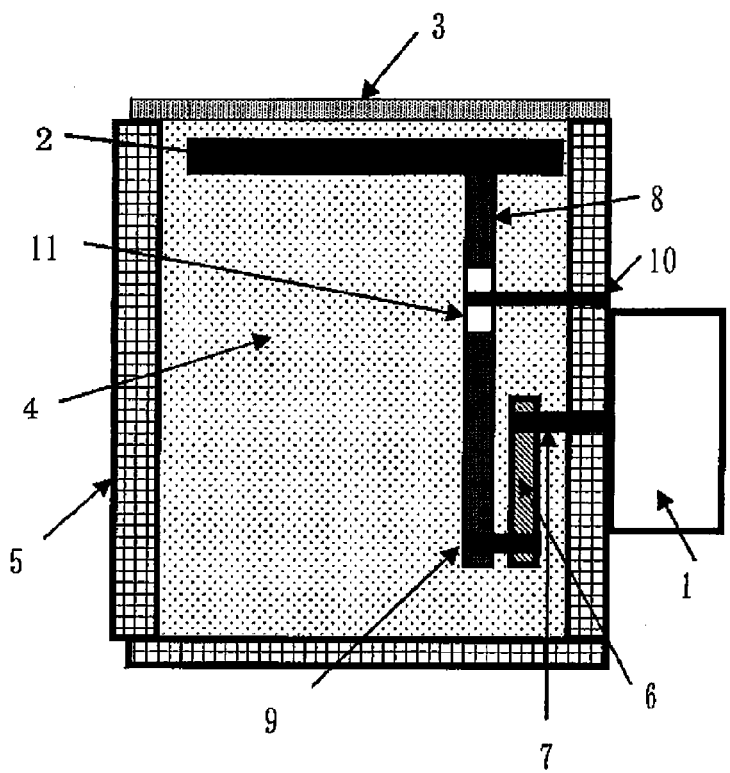
FIG. 1 is a side view of an ultrasonic probe in a first embodiment of the present invention.

Referring to the attached drawings, description will be given below on embodiments of the invention. FIG. 1 shows a side view of an ultrasonic probe in a first embodiment of the invention. In case a speed reducing mechanism is provided on a rotating shaft of a motor 1 or on the motor 1, which is fixed on a frame of the ultrasonic probe, an output shaft of the speed reducing mechanism (hereinafter referred as "a rotating shaft 7") penetrates the frame 5 of the probe, and it is rotated in normal or reverse direction at a predetermined angle in an acoustic coupling liquid 4 to promote propagation of ultrasonic waves sealed by oil-seal or window by means of a driving electric signal from an ultrasonic diagnostic apparatus main unit (not shown), which is connected by an ultrasonic probe. Specifically, a first arm 6 with its one end fixed on a rotating shaft 7, i.e. a first shaft member, is rotated in normal or reverse direction at a predetermined angle around the rotating shaft 7 along with the rotation of the rotating shaft 7, resulting in swinging movement. A coupling shaft 9 is fixed on the other end of the first arm 6, and a second arm 8 is rotatably connected with a coupling shaft 9. At the tip of the other end of the second arm 8, an element unit 2 with an ultrasonic element is disposed, which can convert electric signals and ultrasonic signals with each other. Between the ultrasonic element and the ultrasonic diagnostic apparatus main unit, electric signals are transmitted via a flexible printed circuit board (not shown). On the coupling shaft 9, the first arm 6 and the second arm 8 are rotatably connected respectively. The coupling shaft 9 is fixed either on the first arm 6 or on the second arm 8 so that each arm is rotatable. A lengthwise long groove 11 is formed between a fixed end where the element unit 2 of the second arm 8 is mounted and the coupling shaft 9, and a fixing shaft 10, which is a second shaft member fixed on the probe frame 5, is engaged with the groove 11. The width of the groove 11 is approximately the same as diameter of the engaging unit of the fixed shaft 10. It is designed as a lengthwise long groove in a direction of the length of the second arm 8. The length of the groove would suffice if the second arm 8 can move when the rotating shaft 7 is rotated in normal or reverse direction. With the rotation in normal or reverse direction of the first arm 6, the second arm 8 can be moved in the direction of the length along the lengthwise long groove 11.

The first arm 6 fixed on the rotating shaft 7 of the motor 1 rotates the second arm 8, which is rotatably fixed by the coupling shaft 9 due to the swinging movement caused by the rotation in normal or reverse direction of the rotating shaft 7 with the fixed shaft 10 as fulcrum, and the element unit 2 performs swinging movement with the fixed shaft 10 as fulcrum. In this case, the element unit 2 mounted on the second arm 8 moves along the groove 11, which is engaged with the fixing shaft 10, the second arm 8 is engaged with the fixed shaft 10 in the direction of length when the first arm 6 is rotated along with the rotation of the rotating shaft 7 due to the movement of the coupling shaft 9. As a result, the locus, along which the element unit 2 moves, is different from the locus when the coupling shaft 9 of the second arm 8 is used as the rotating shaft for fixing.

Figure 2:
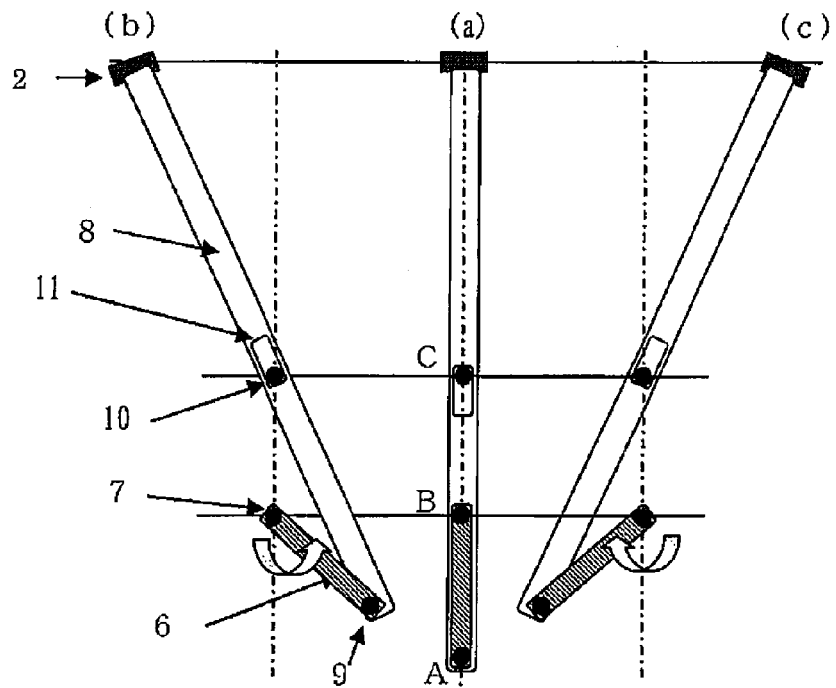
FIG. 2 is a schematical drawing to explain a swinging mechanism to be used in the ultrasonic probe shown in FIG. 1.

FIG. 2 is a drawing, schematically showing operation of the swinging mechanism, which comprises a first arm 6 and a second arm 8, according to the present invention. Referring to FIG. 2, detailed description will be given below on the swinging rotation.

When the rotating shaft 7 of the motor is rotated in normal direction or in reverse direction, the first arm 6 with its one end fixed on the rotating shaft 7 is also rotated in normal direction or in reverse direction. It is supposed here that the other end (not fixed on the rotating shaft 7) of the first arm 6 is at a point A, that the rotating shaft 7 is a point B, and that the fixed shaft 10 engaged in the groove 11 of the second arm 8 is a point C. Then, swinging is performed so that a triangular shape is always formed by the points A, B and C. According to the direction of the rotation of the coupling shaft 9, the coupling shaft 9 is swung from FIG. 2 (a) to FIG. 2 (b), or from FIG. 2 (a) to FIG. 2 (c). As a result, the larger the rotation angle of the rotating shaft 7 of the motor is, the more the coupling shaft 9, which is an operating point of the second arm 8, is rotated so that the element unit 2 is extended in the length direction. The locus of the moving of the element unit 2 will be the locus of the curvature, which is different from the case where the coupling shaft 9 of the second arm 8 is the center of the swinging. Thus, by using a simple swinging mechanism, the element unit 2 having the ultrasonic element can be moved with larger curvature. Accordingly, even when diagnosis is made on a relatively flat affected region of the patient, the adhesiveness with the ultrasonic probe can be increased.

Figure 3:
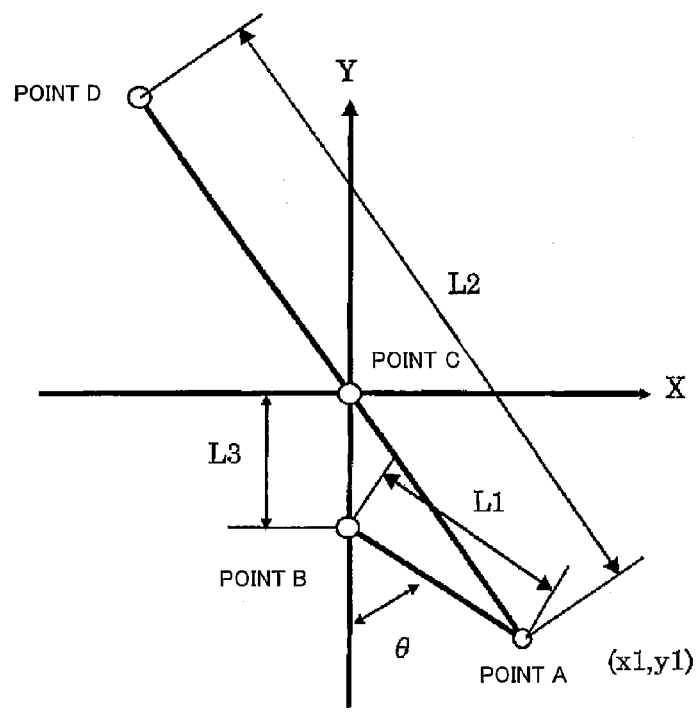
FIG. 3 is a schematical drawing to explain a principle of the swinging mechanism to be used on the ultrasonic probe shown in FIG. 1.

FIG. 3 is a drawing to explain the principle of the swinging mechanism, which comprises the first arm 6 and the second arm 8. Referring to FIG. 3, detailed description will be given on the locus of the element unit 2 when the rotating shaft 7 of the motor is rotated in normal direction or in reverse direction.

Coordinates X-Y are taken with a fixed shaft 10 (Point C) as the origin, and it is supposed that a distance between the motor rotating shaft 7 (Point B) and the coupling shaft 9 (Point A) of the first arm 6 is L1, that a distance between the coupling shaft 9 (Point A) and the tip (Point D) of the element unit 2 of the second arm 8 is L2, that a distance between the motor shaft 7 (Point B) and the fixed shaft 10 (Point C) is L3, and that L2 is sufficiently longer than L1 and L3. When the first arm 6 is tilted at a swinging angle of θ with respect to Y axis, the coordinates of the Point A, which is the connecting point of the first arm 6 and the second arm 8 is given as:

$$(L1 \times \sin\theta; -L1 \times \cos\theta - L3)$$

And the second arm 8 will be on a straight line:

$$Y = -((L1 \times \cos\theta - L3)/L1 \times \sin\theta)X$$

in the coordinates X-Y with the fixed shaft 10 (Point C) as the origin.

Therefore, a distance DL from the origin (Point C) to the connecting point (Point A) of two arms is given as:

$$\sqrt{(L1 \times \sin\theta) \times (L1 \times \sin\theta) + (-L1 \times \cos\theta - L3)(-L1 \times \cos\theta L3)} = \sqrt{L1 \times L1 + L3 \times L3 + 2\cos\theta \times L3 \times L1} \quad \text{[Equation 1]}$$

Therefore, the coordinates of the Point D, which is the tip of the second arm 8, is given as:

$$(-L1 \times \sin\theta \times (L2-DL)/DL; (L1\cos\theta + L3) \times (L2-DL)/DL)$$

Figure 4:
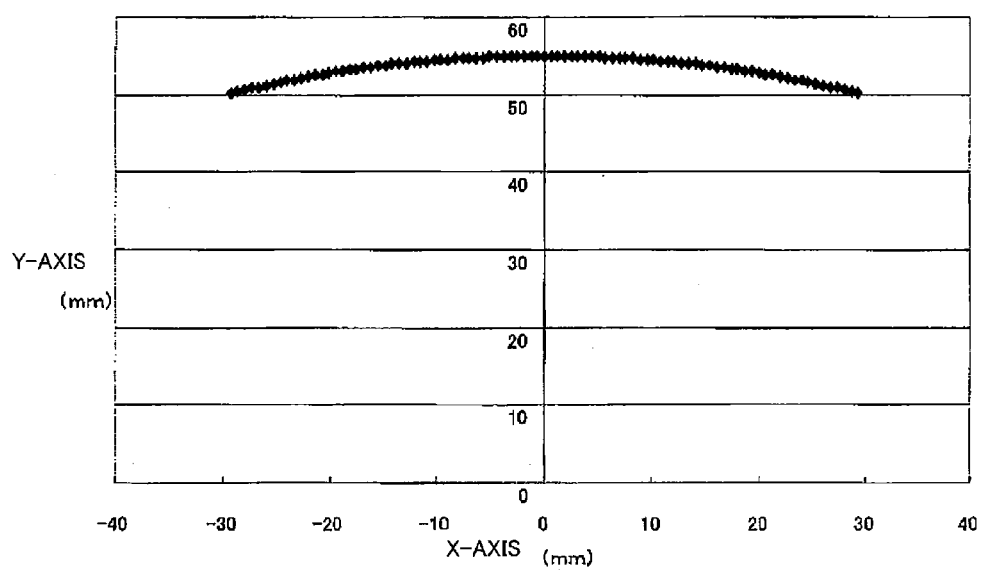
FIG. 4 is a graphic diagram to show an example of locus of swinging of an element unit to be used in the ultrasonic probe shown in FIG. 1.

FIG. 4 is a drawing to show the locus of the tip point D of the second arm 8 when it is supposed that L1=30 mm, L2=100 mm and L3=15 mm, and that the first arm 6 is swung up to ±45° from Y axis. It shows a convex type locus with larger curvature.

Figure 5:
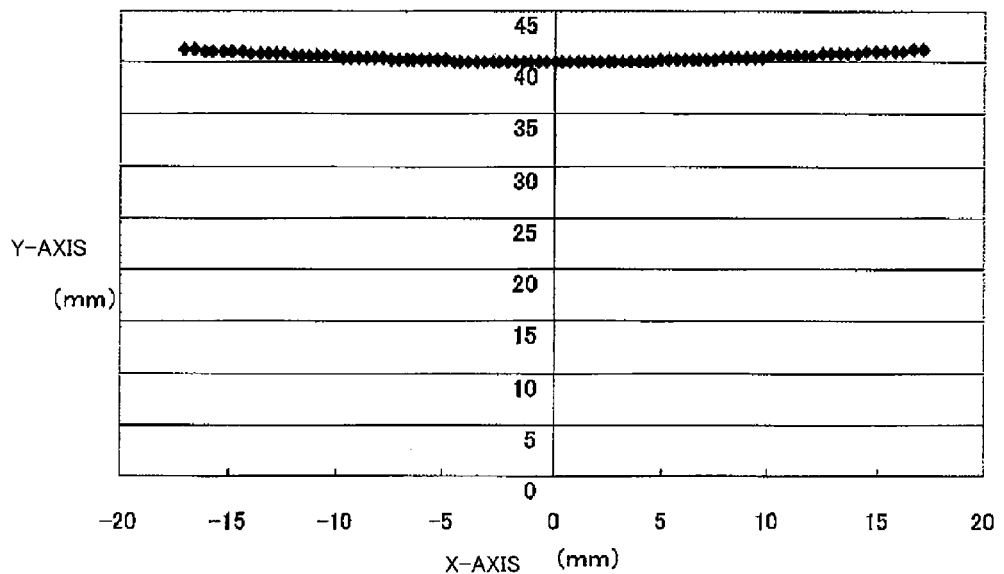
FIG. 5 is a graphic diagram to show another example of locus of swinging of an element unit to be used in the ultrasonic probe shown in FIG. 1.

FIG. 5 shows the locus of the tip point D of the second arm 8 in case it is supposed that L1=30 mm, L2=100 mm, and L3=30 mm, and that the first arm 6 is swung from Y axis up to an angle of ±45°. It shows an approximately flat locus although it is slightly concaved.

The locus of the tip of the second arm 8 shown in FIG. 4 and FIG. 5 is merely an example. By adjusting the length of each of L1, L2 and L3 respectively, it is possible to have the locus of the tip point D of the second arm 8 as desired.

Figure 6:
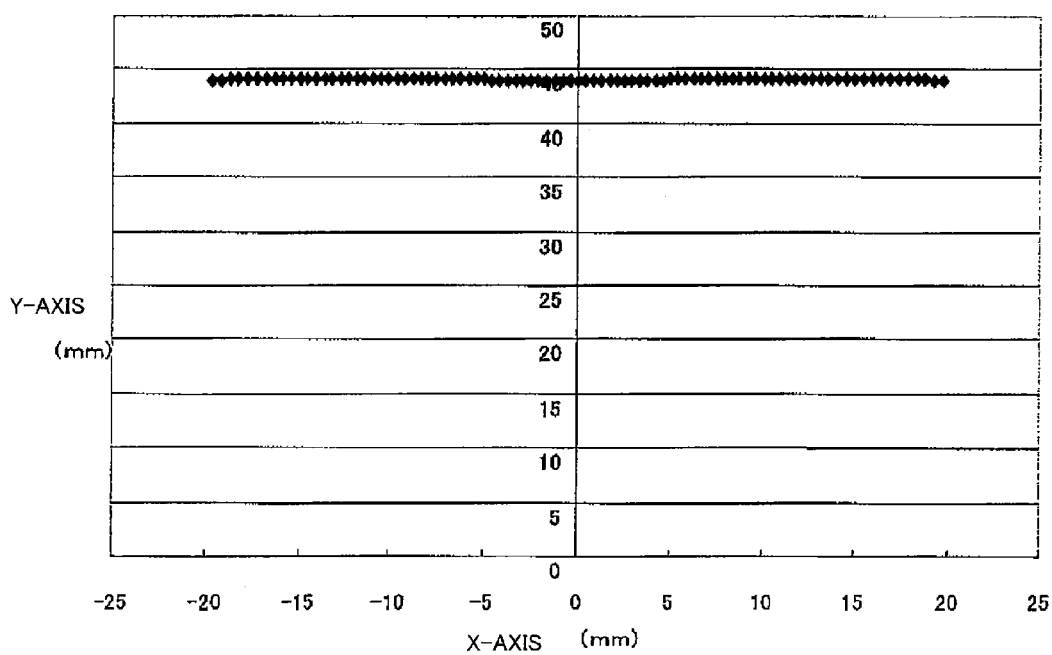
FIG. 6 is a graphic diagram to show still another example of locus of swinging of an element unit to be used in the ultrasonic probe shown in FIG. 1.

FIG. 6 shows the locus of the tip point D of the second arm when it is supposed that L1=30 mm, L2=100 mm, and L3=26 mm, and that the first arm 6 is swung from Y-axis up to an angle of ±45°. As shown in this figure, the displacement in the direction of Y-axis can be set at about 0.1 mm, and the element unit 2 can be moved in approximately horizontal direction.

Also, in case a distance from the Point A to the Point B is made equal to the distance between the Point B and the Point C in FIG. 3, the triangle ABC can be formed as an isosceles triangle at all times. If the triangle ABC is an isosceles triangle, there exists a relation: $2\angle ACB=\theta$. With respect to the rotation angle $\theta$ of the first arm 6, the rotation angle of the element unit 2 is tilted at an angle of one half at all times. Thus, the swinging angle of the ultrasonic element can always be maintained at a relation of 2:1 to the rotation angle of the motor. If the rotation angle of the motor is swung at a constant angle, the ultrasonic element can always have uniform swinging angle.

Figure 7:
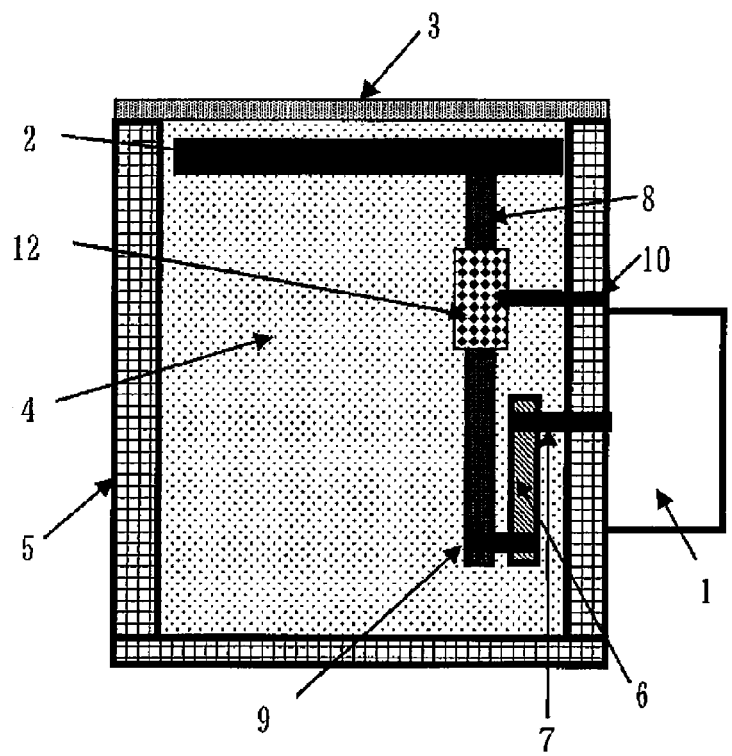
FIG. 7 is a side view of an ultrasonic probe in a second embodiment of the invention.

FIG. 7 is a side view of an ultrasonic probe in the second embodiment of the invention. Instead of the engagement of the fixed shaft 10 with the groove 11 of the second arm 8 as shown in FIG. 1, a slide bearing 12 is mounted on the second arm 8 to be connected with the fixed shaft 10 to ensure smooth moving of the second arm 8 in this embodiment. Also, it may be so designed that two or more bearings are provided at the tip of the fixed shaft 10 to be engaged with the groove 11 in the embodiment shown in FIG. 1 in order to ensure smooth moving. In this case, it is desirable to have such an arrangement that shakiness can be absorbed by means of a spring to overcome the variation of groove width caused by fabrication accuracy of the groove 11 by two or more bearings.

Figure 8:
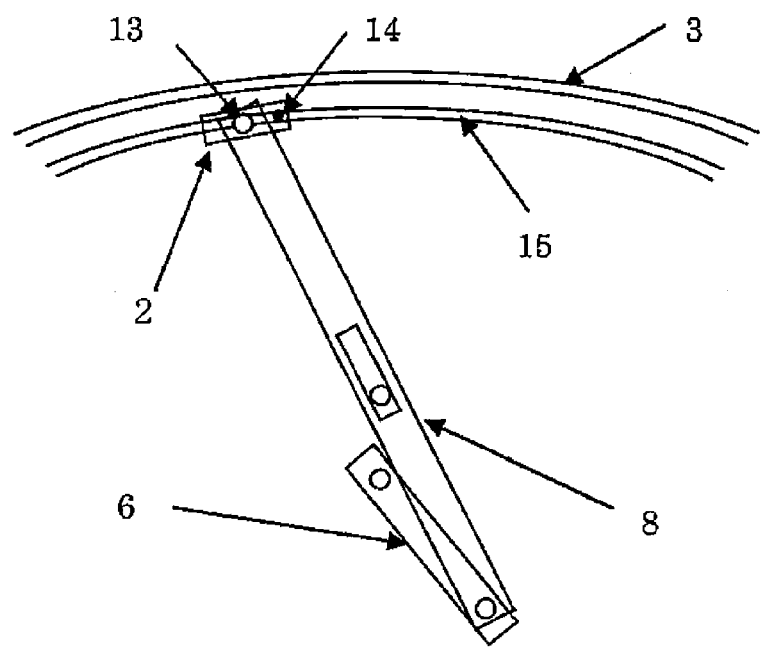
FIG. 8 is a drawing to show connection of an element unit in the first embodiment of the ultrasonic probe of the invention.

FIG. 8 shows the condition of the connection of the element unit in the first embodiment of the ultrasonic probe according to the invention. In this embodiment, the element unit 2 with the ultrasonic element attached on the tip of the second arm 8 is rotatably mounted on the tip of the second arm 8 via an element rotating shaft 13, and a guiding shaft 14 mounted on the element unit 2 is engaged with a groove type rail 15 mounted on the probe frame 5 or on a window 3. The element unit 2 can move along the rail 15 by means of the guiding shaft 14, and the ultrasonic element to transmit and receive the ultrasonic waves can be tilted in any direction as desired with respect to the body of the patient. Also, by this arrangement, the ultrasonic element can always be kept in parallel to the window 3. As a result, the ultrasonic waves emitted from the ultrasonic element can be always projected perpendicularly to the surface of the window 3.

Figure 9:
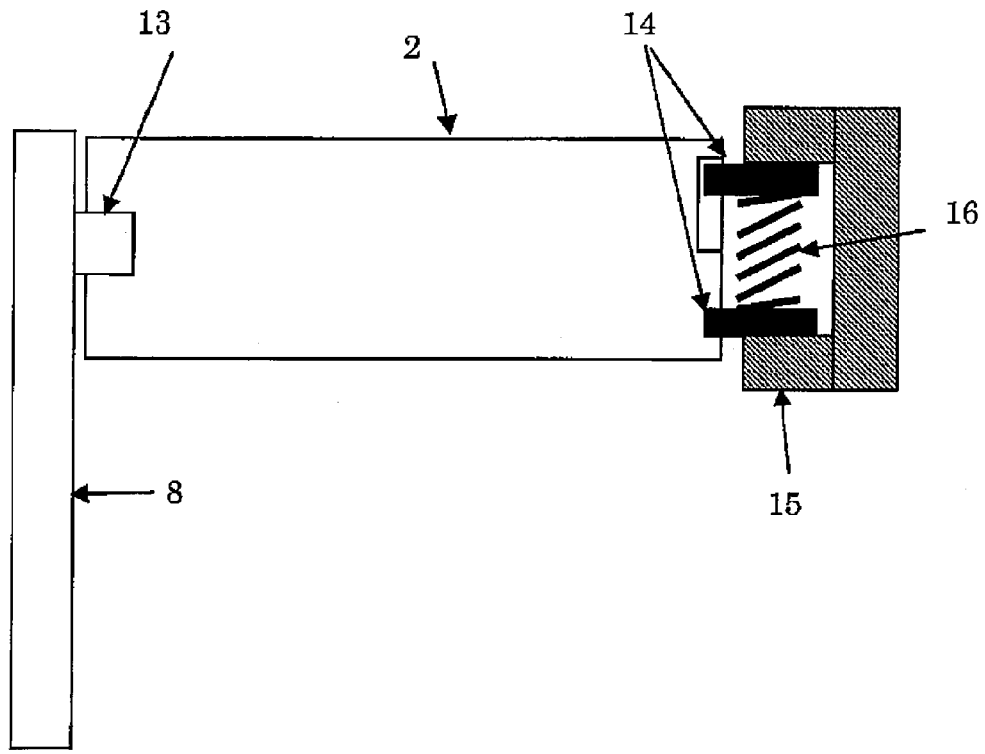
FIG. 9 is a drawing to show a connecting structure of an element unit of the ultrasonic probe shown in FIG. 8.

FIG. 9 shows a connecting structure of the element unit of the ultrasonic probe shown in FIG. 8. The guiding shaft 14 has two guiding shafts. One of the guiding shafts is fixed on the element unit 2, and the other guiding shaft is fixed on a spring 16, and the groove type rail 15 and the two guiding shafts 14 are engaged with each other by resilient force of the spring 16. As a result, the shakiness between the groove of the rail 15 and the guiding shaft 14 caused by fabrication accuracy of the component parts can be absorbed. This contributes to the reduction of vibration and noise during operation and is also helpful to stabilize the tilting angle of the element unit 2 during the swinging operation.

Figure 10:
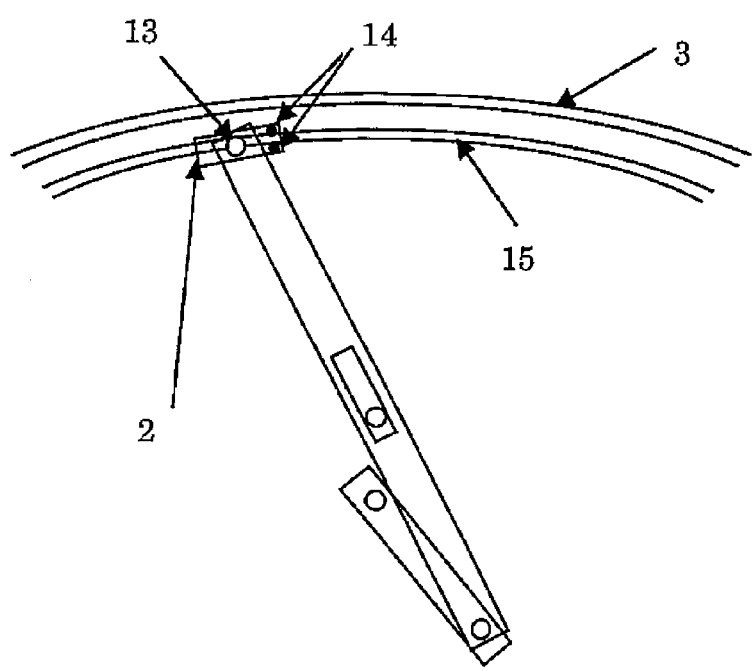
FIG. 10 is a schematical drawing to show a connection of an element unit in the first embodiment of the ultrasonic probe of the invention.

FIG. 10 is a drawing to show connection of the element unit in the first embodiment of the ultrasonic probe of the invention. A convex type rail 15 is placed between two guiding shafts 14 to support the element unit 2. By this arrangement, ultrasonic waves can be projected perpendicularly to the surface of the window 3. Compared with the case where concave grooves are formed on the window 3 or on the probe frame 5, this makes it easier to fabricate the rail 15 by mechanical fabrication or by die molding. The number of the guiding shafts 14 is not limited to two, and three or more guiding shafts 14 may be used to support the element unit 2.

Figure 11:
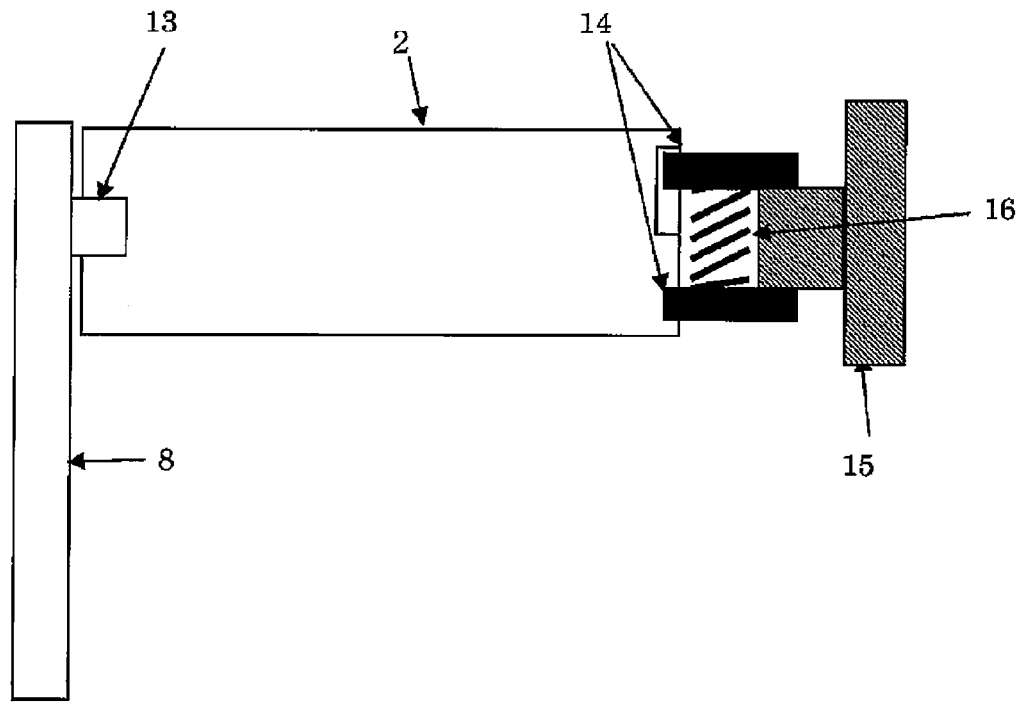
FIG. 11 is a schematical drawing to show a connecting structure of an element unit in a first modification of the ultrasonic probe shown in FIG. 10.

FIG. 11 is a drawing to show a connecting structure in a first modification of the element unit of the ultrasonic probe shown in FIG. 10. The guiding shafts 14 comprise two guiding shafts. One of the guiding shafts is fixed on the element unit 2, and the other of the guiding shafts is fixed on the spring 16. By resilient force of the spring 16, convex portion of the rail 15 inserted between the two guiding shafts is pressed together. By this arrangement, the shakiness of the convex type rail 15 and the two guiding shafts 14 originated from the causes such as the lack of fabrication accuracy can be absorbed by the spring 16, and vibration and noise during operation can be reduced. At the same time, tilting angle of the element unit 2 can be stabilized during swinging operation. Also, when the rail 15 is manufactured by mechanical fabrication or by die molding, manufacturing procedure will be much easier compared with the case where the groove should be fabricated.

Figure 12:
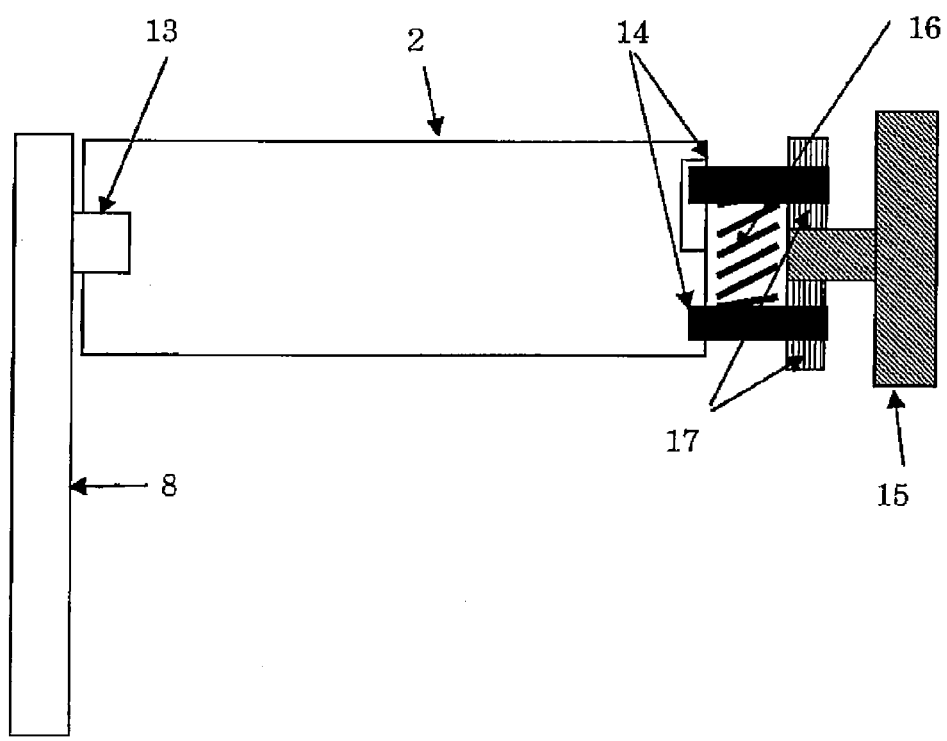
FIG. 12 is a drawing, schematically showing a connecting structure in a second modification of the element unit of the ultrasonic probe shown in FIG. 10.

FIG. 12 is a drawing to show a connecting structure in a second modification of the element unit of the ultrasonic probe shown in FIG. 10. In addition to the embodiment shown in FIG. 11, bearings 17 are mounted at forward ends of two guiding shafts 14, and the guiding shafts 14 are pressed together to the convex part of the rail 15 via the bearings 17 by resilient force of the spring 16. By this arrangement, sliding friction resistance between the rail 15 and the guiding shaft 14 can be decreased, and this contributes to the reduction of the burden on the motor 1 to be driven, and smooth movement can be accomplished. Instead of the use of the bearings 17, if low-friction materials such as Teflon resin may be used at the forward ends of the two guiding shafts 14 to slide over the convex portion of the rail 15, the same effects can be attained. If necessary, without providing the spring 16, only the bearings or the low friction materials such as Teflon resin may be used.

Figure 13:
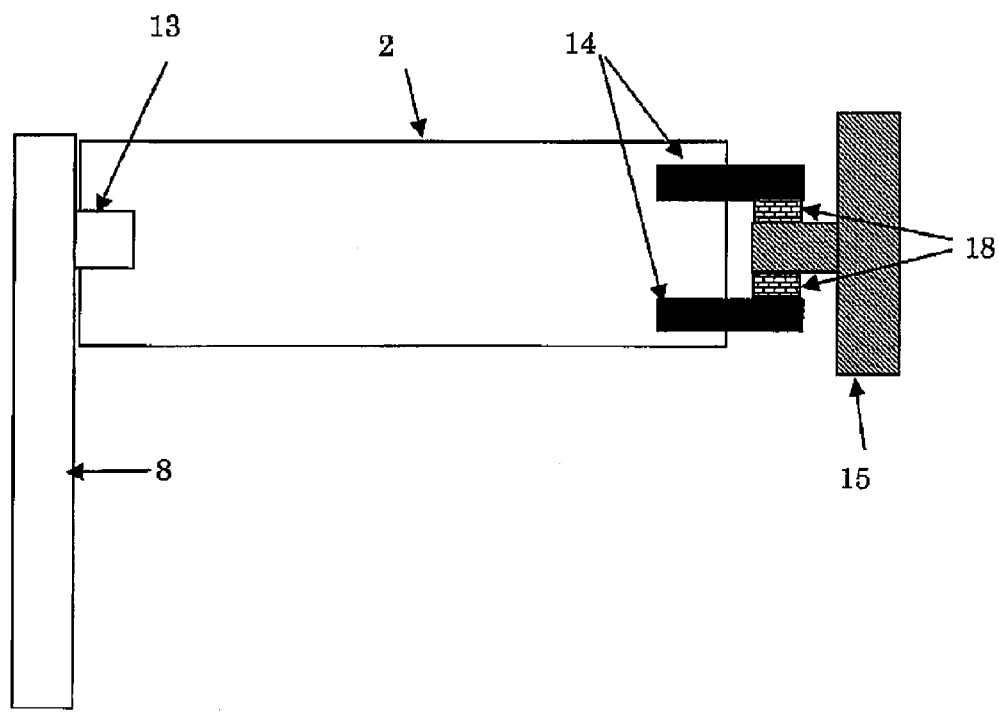
FIG. 13 is a drawing, schematically showing a connecting structure in a third modification of the element unit of the ultrasonic probe shown in FIG. 10.

FIG. 13 is a drawing to show a connecting structure in the third modification of the element unit of the ultrasonic probe shown in FIG. 10. An elastic member 18 is disposed at the tips of two guiding shafts 14, and the elastic members 18 are pressed to the convex portion of the rail 15. By this arrangement, even when there is variation in thickness of the convex portion squeezed by the guiding shafts 14 of the convex rail 15, the shakiness caused can be absorbed by the elastic members 18, and it is possible to reduce vibration noise and to accomplish the movement with lower load variation. One of the two guiding shafts 14 may be used as the elastic member 18.

Figure 14:
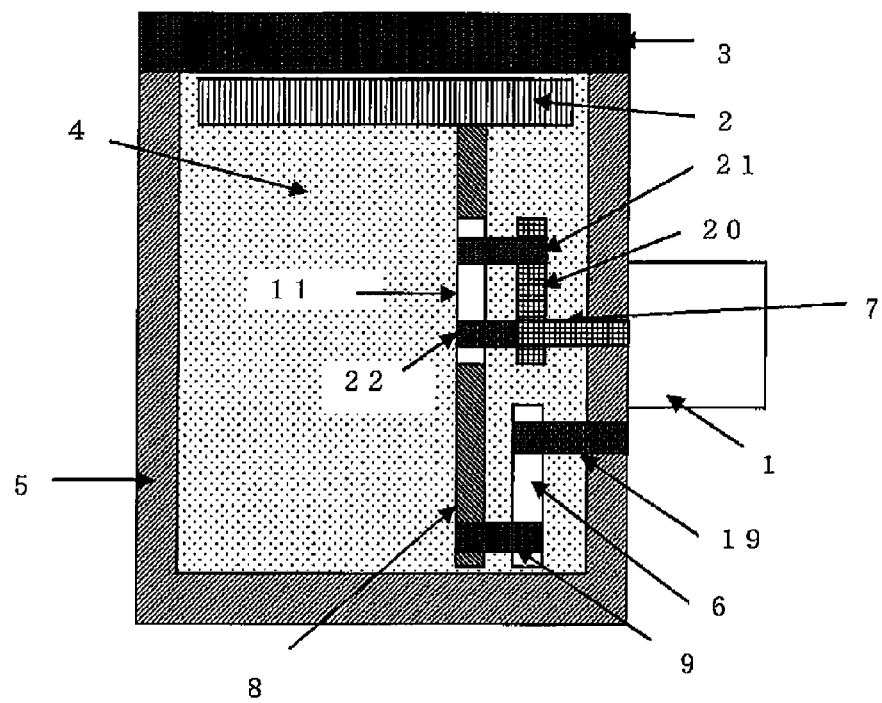
FIG. 14 is a side view showing the ultrasonic probe in the third embodiment of the invention.

FIG. 14 is a side view of an ultrasonic probe in the third embodiment of the invention. The first arm 6 is rotatably mounted around the fixed shaft 19, which is a first shaft member. On the rotation shaft 7 fixed on the motor 1, a third arm 20 is mounted, and it is rotated in normal or reverse direction at a predetermined angle around the rotating shaft 7 in association with the normal or reverse rotation of the rotating shaft 7. On the third arm 20, a first driving shaft 21 and a second driving shaft 22 are fixed. The second driving shaft 22 may be disposed along a line, which connects the driving shaft 21 with the rotating shaft 7. FIG. 14 shows the case where it is disposed on the axis of the rotating shaft 7. Specifically, the first driving shaft 21, the second driving shaft 22 and the coupling shaft 9 are always positioned along the same straight line. Thus, the rotation of the first arm 6 in reverse direction can be avoided when the first driving shaft 21 is rotated. The rotating shaft 7, the third arm 20, the first driving shaft 21, and the second driving shaft 22 make up together a second shaft member.

The first driving shaft 21 and the second driving shaft 22 are engaged with the groove 11, which is disposed on the second arm 8. The width of the groove 11 is approximately the same as diameter of the first driving shaft 21 and the second driving shaft 22, and it is formed lengthwise long along the direction of the length of the second arm 8. By normal or reverse rotation of the rotating shaft 7, the second arm 8 can be moved in swinging movement via the first driving shaft 21 and the second driving shaft 22.

The first arm 6, the coupling shaft 9, and the second arm 8 make up together a linking mechanism. When the rotating shaft 7 is rotated in normal or reverse direction via this linking mechanism, it can be moved in swinging movement with a radius curvature longer than the length of the second arm 8. In this case, the third arm 20, the first drive shaft 21 and the second drive shaft 22 may be provided separately or may be integrated together.

Figure 15A:
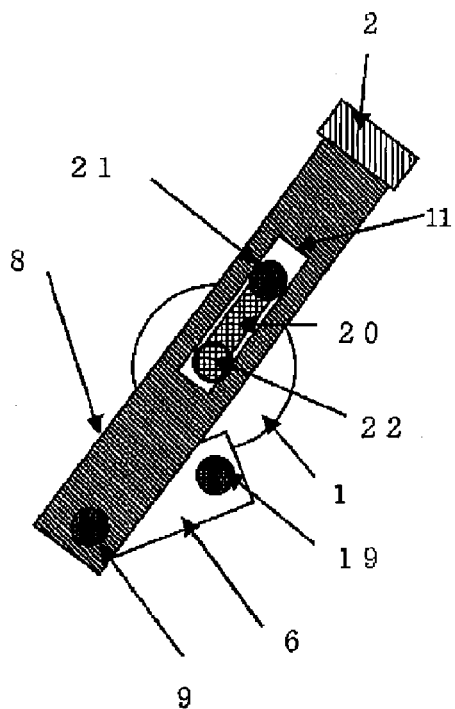
FIG. 15A is a schematical drawing to show operation of the swinging mechanism to be used in the ultrasonic probe shown in FIG. 14 as it is at a position tilted rightward.
Figure 15B:
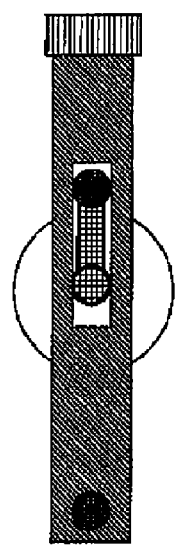
FIG. 15B is a schematical drawing to show operation of the swinging mechanism to be used in the ultrasonic probe shown in FIG. 14 as it is at its central position.
Figure 15C:
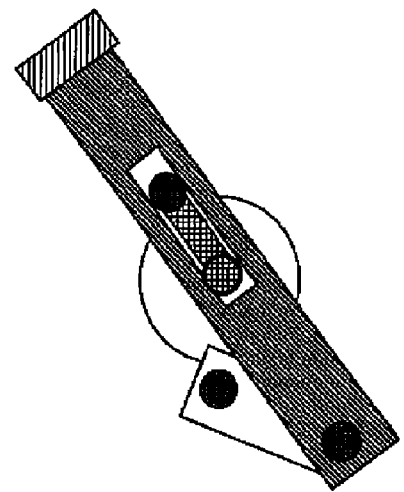
FIG. 15C is a schematical drawing to show operation of the swinging mechanism to be used in the ultrasonic probe shown in FIG. 14 as it is at a position tilted leftward.

FIG. 15A to FIG. 15C represent the drawings, each showing the swinging mechanism, which comprises the first arm 6 and the second arm 8 at the rightward tilted position, at the central position, and at the leftward tilted position in the third embodiment respectively. Referring to FIG. 15A to FIG. 15C, detailed description will be given below on the swinging rotation.

When the rotating shaft 7 is rotated in normal or reverse direction, the third arm 20 with its one end fixed on the rotating shaft 7 is also rotated in normal or reverse direction. FIG. 15A shows a condition where the rotating shaft 7 is rotated and the element unit 2 is tilted rightward. Here, if it is supposed that the center of the rotating shaft 7 is the Point A, when the rotating shaft 7 is rotated, the third arm 20 fixed on the rotating shaft 7 is rotated around the Point A. A fixed shaft 19 is disposed at a certain distance from the rotating shaft 7. If it is supposed that the center of the fixed shaft 19 is the Point B, one end of the first arm 6 is rotatably held around the Point B. The other end of the first arm 6 is rotatably connected with the second arm 8 via the coupling shaft 9. If it is supposed that the center of the coupling shaft 9 is the Point C, it is swung so that the Point A, the Point B and the Point C always form a triangle. On the second arm B, a lengthwise long groove 11 is provided in the direction of the length. The tips of the first driving shaft 21 and the second driving shafts 22 provided on the third arm 20 are engaged with this groove 11, and the second arm 8 can move in the length direction.

The second arm 8 is always swung in such direction that a triangle is formed by the Point A, the Point B, and the Point C. According to the direction of the rotation of the rotating shaft 7, it is swung as shown from FIG. 15A, to FIG. 15B and to FIG. 15C. The bigger the rotation angle of the rotating shaft 7 of the motor is, the more the second arm 8 is extended and the element unit 2 is rotated in the length direction by the coupling shaft 9, which is an operating point of the second arm 8.

Here, by defining the first driving shaft 21 as a Point D, and when the first driving shaft 21 and the second driving shaft 22 are engaged with the groove 11 and are rotated, the second arm 8 is positioned with its lower end at the Point C, and the tilting is determined by the Point C and the Point D, and swinging is performed. As a result, the moving locus of the element unit 2 will be a locus with a larger curvature than the case where the center of the swinging is on the coupling shaft 9 of the second arm 8.

Figure 16:
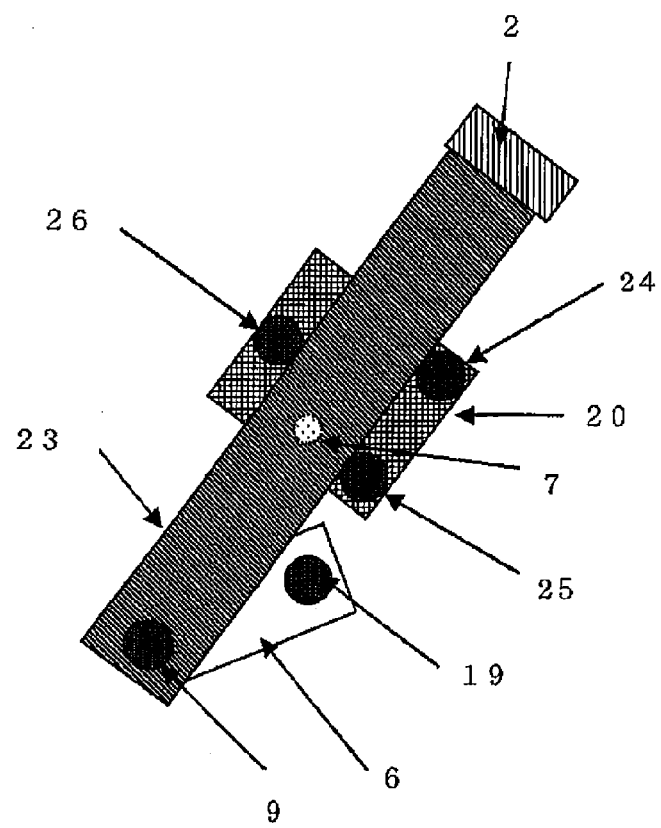
FIG. 16 is a schematical drawing to explain operation of the swinging mechanism to be used in the ultrasonic probe in a fourth embodiment of the invention.

FIG. 16 is a drawing to explain operation of a swinging mechanism, which has a first arm 6 and a fourth arm 23 in the fourth embodiment of the invention. Referring to FIG. 16, detailed description will be given on the swinging rotation.

Specifically, in the fourth embodiment, it is not an arrangement where the groove 11 is provided on the second arm 8 as described above and it is swung, but it is so arranged that a first sliding shaft 24, a second sliding shaft 25, and a third sliding shaft 26 are provided on the third arm 20, and the fourth arm 23 is squeezed between them. The fourth arm 23 can be swung by rotating the third arm 20 in normal or reverse direction. As a result, the moving locus of the element unit 2 will be a locus having a larger curvature than the case where the coupling shaft 9 of the fourth arm 23 is set as the center of swinging. In this case, it may be so arranged that the first sliding shaft 24, the second sliding shaft 25, and the third sliding shaft 26 may be brought into contact with the fourth arm 23 by means of bearing or resin with low friction resistance to reduce the sliding resistance with the fourth arm 23. Further, in order to prevent the shakiness, it may be so designed that the third sliding shaft 26 is pulled toward the first sliding shaft 24 and the second sliding shaft 25 by means of spring or elastic material.

Figure 17:
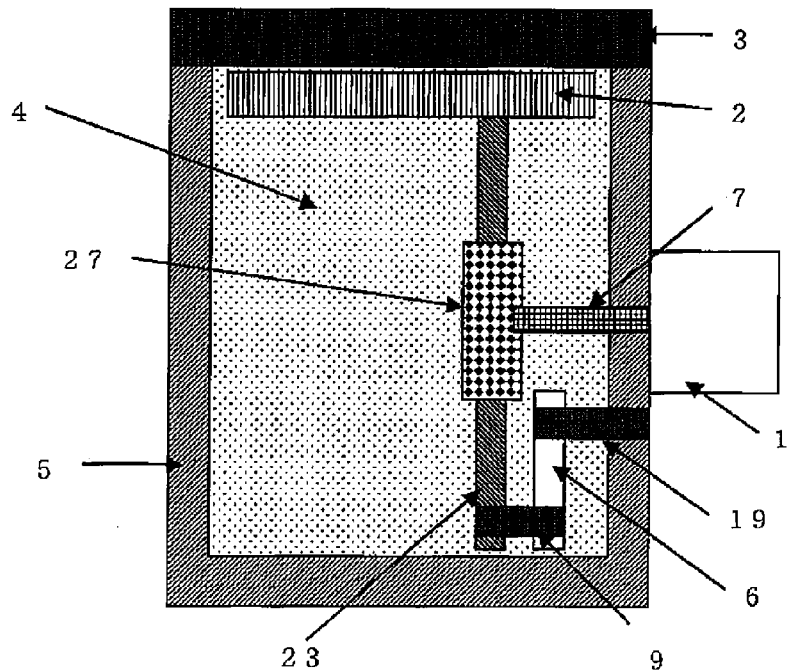
FIG. 17 is a side view of an ultrasonic probe in a fifth embodiment of the invention.

FIG. 17 is a side view of the ultrasonic probe in the fifth embodiment of the invention, and a slide bearing 27 engaged with the fourth arm 23 is mounted on the rotating shaft 7. In association with normal rotation or reverse rotation of the rotating shaft 7, the fourth arm 23 is swung inside of the slide bearing 27.

Figure 18:
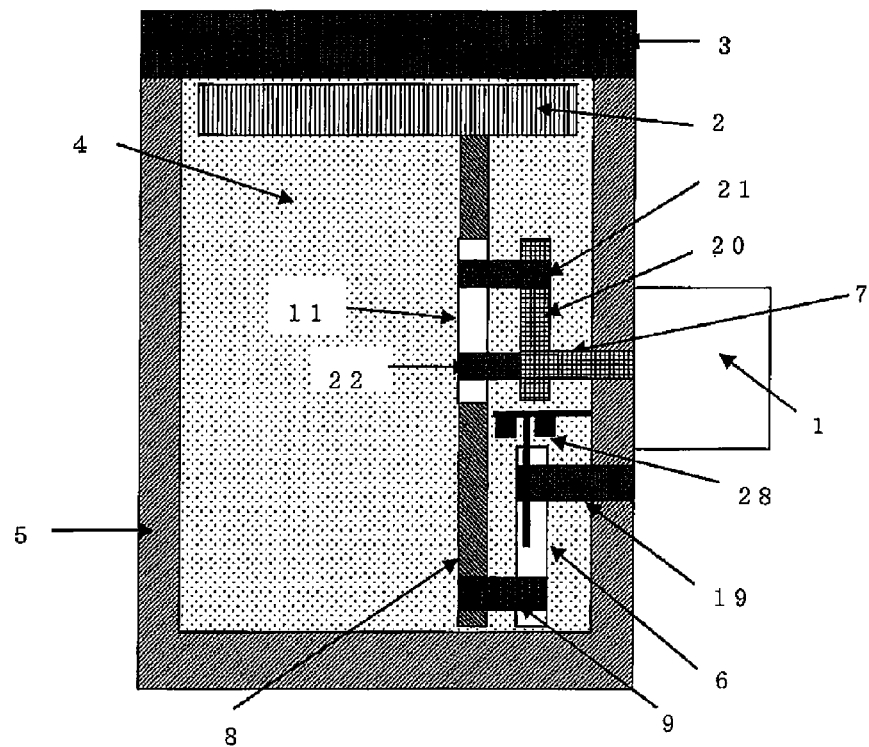
FIG. 18 is a side view of an ultrasonic probe in a sixth embodiment of the invention.
Figure 19:
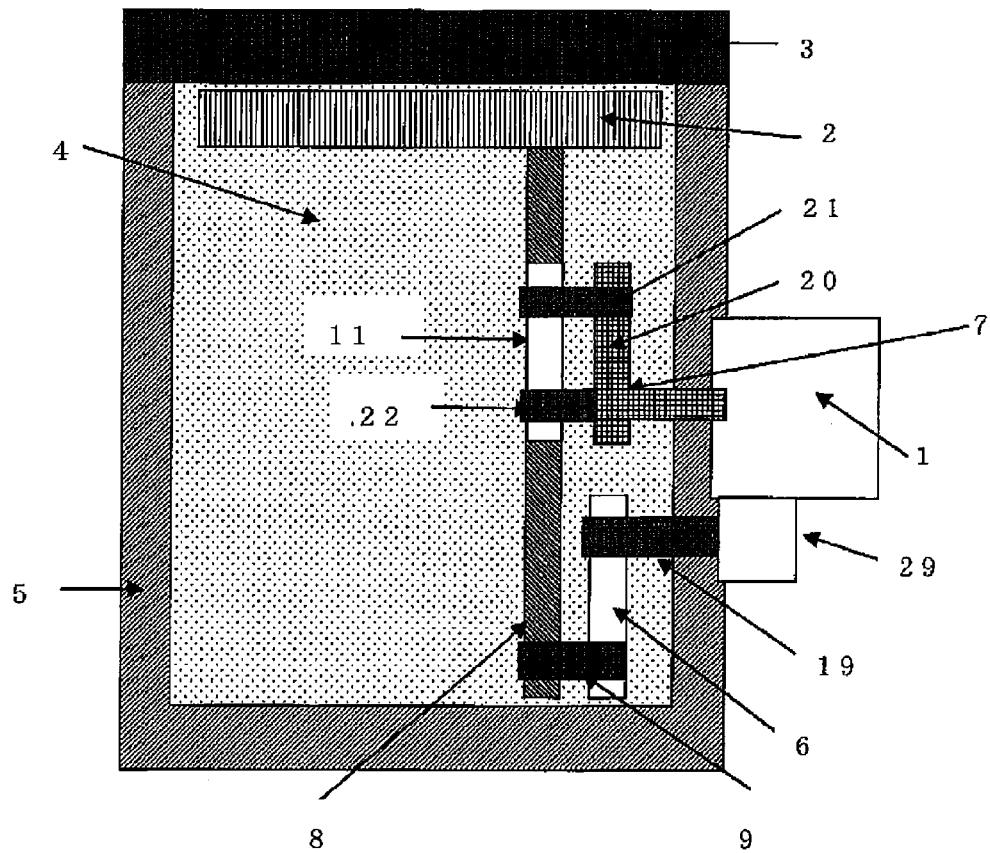
FIG. 19 is a side view of an ultrasonic probe in a seventh embodiment of the invention.
Figure 20:
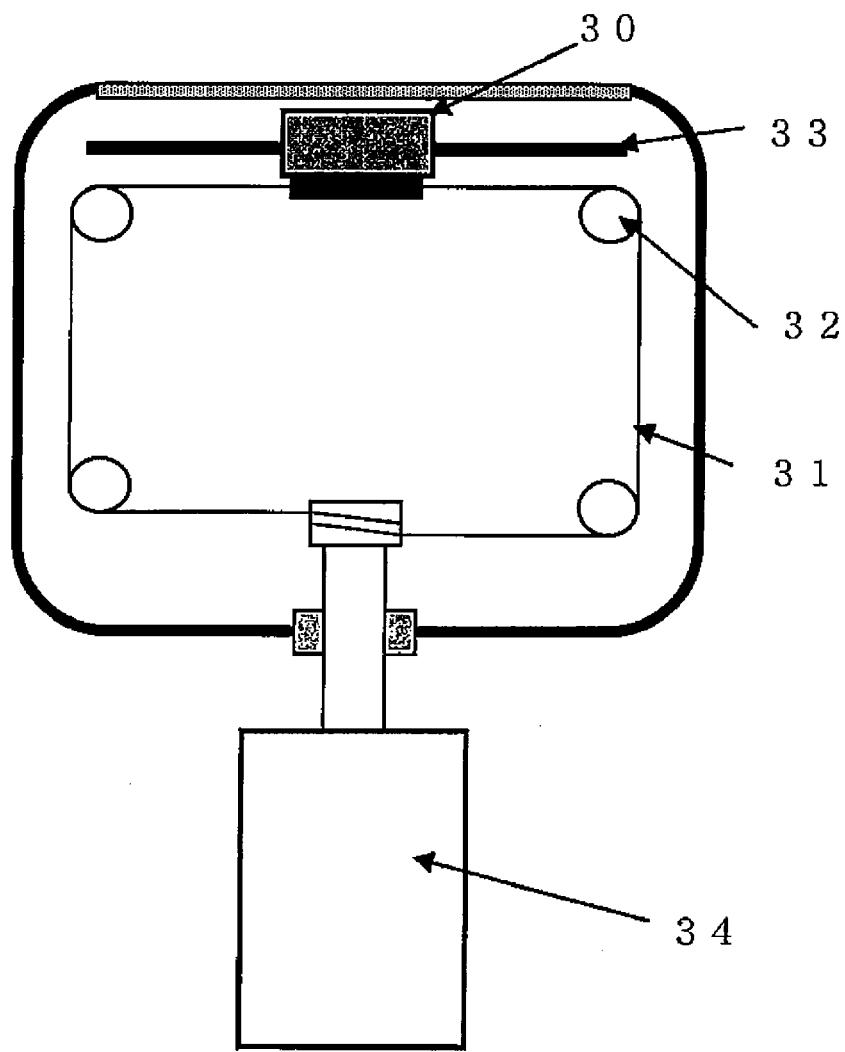
FIG. 20 represents a drawing to give a configuration of an ultrasonic probe according to the prior art.
Figure 21:
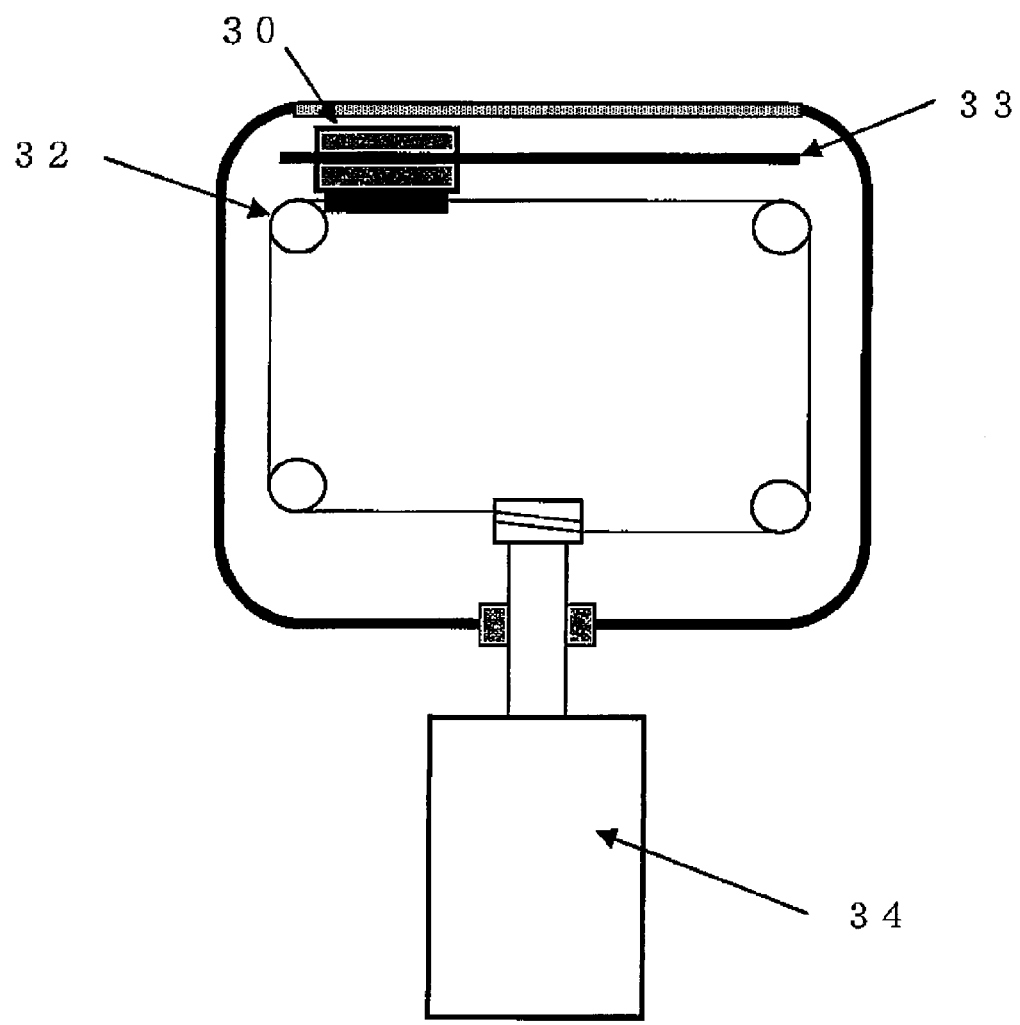
FIG. 21 is a schematical drawing to show a configuration of another ultrasonic probe of the prior art.

FIG. 18 is a side view of the ultrasonic probe in the sixth embodiment of the invention, and FIG. 19 is a side view of the ultrasonic probe in the seventh embodiment of the invention. In FIG. 18, position detecting means 28 for detecting rotation angle of the first arm 6 is disposed inside the probe frame 5. FIG. 19 shows an arrangement where the fixed shaft 19 and the arm 6 are integrated and are rotated together, and it penetrates the frame 5 rotatably, and position detecting means 29 is provided outside the probe frame 9 to detect a rotation angle of the first arm 6 via a fixed shaft 19.

It is supposed here that the center of the rotating shaft 7 is the Point A, the center of the fixed shaft 19 is the Point B, and the center of the coupling shaft 9 is the Point C.

Then, by arranging that a distance from the Point A to the Point B is the same as the distance between the Point B and the Point C, the triangle ABC is always formed as an isosceles triangle. If the third arm 20 is rotated by an angle θ, the tip of the second arm 8 is rotated by an angle θ around a virtual rotation center, and the first arm 6 is rotated at an angle of 2θ. That is, by detecting the rotation angle of the first arm 6, which is rotated at an angle twice as large as the rotation angle of the rotation shaft 7, i.e. a tilting angle of the element unit 2 by means of the position detecting means 28 or 29, the tilting angle of the element unit 2 can be detected with high accuracy. As the position detecting means 28 and 29, an optical encoder or a magnetic encoder or a potentiometer can be used.

As the connecting structure of the element unit 2 in the third to the seventh embodiments as given above, the connecting structure as shown in FIG. 8 to FIG. 13 can be applied.

As described above, according to the present invention, an apparent rotation radius of the moving of the ultrasonic element can be set to a larger value, and this makes it possible to design the ultrasonic element in smaller size. Also, as described above, when the ultrasonic element is moved by using wire and pulley as in the conventional example given above, there is a region, which comes out beyond both ends from the scanning area as it is necessarily caused by the diameter of the pulley, while, in the arrangement as given above, such problem can be actually eliminated. This contributes to the elimination of dead space, which causes when accurate diagnosis must be performed on the body of the patient.

The ultrasonic element as given above may be a single element, and it may be a mechanical ultrasonic probe, which mechanically scans by means of swinging mechanism. If the ultrasonic element is an electronic scanning type ultrasonic element and if the ultrasonic element is arranged so that electronic scanning is performed in a direction perpendicularly crossing the mechanical swinging direction, it is possible to obtain an ultrasonic probe, which can acquire three-dimensional ultrasonic image through scanning by electronic scanning and the scanning by mechanical swinging.

INDUSTRIAL APPLICABILITY

As described above, the present invention provides such effects that a mechanism can be accomplished, by which it is possible to have higher radius of curvature so that the contact portion of the probe will be in such shape as to ensure close contact with the body of the patient. The invention provides an ultrasonic probe to acquire ultrasonic tomogram by mechanically swinging the ultrasonic element and a small type ultrasonic probe with higher convenience as a hand-carried ultrasonic probe, and the invention can be applied on mechanical ultrasonic probe or on ultrasonic probe suitable for three-dimensional investigation.

The invention claimed is:

1. An ultrasonic probe, comprising
a cubicle,
a swinging mechanism disposed in the cubicle,
an acoustic coupling liquid sealed in the cubicle,
wherein the swinging mechanism comprising:
a first arm with one end fixed on a first shaft member,
a second arm with one end rotatably connected to the other end of said first arm via a coupling shaft,
an ultrasonic element to mutually convert electric signals and ultrasonic signals provided on the other end of the second arm,
wherein said second arm includes a lengthwise long groove, and a second shaft member is engaged with the groove and slidable in the direction of the length of the groove,
and said ultrasonic element is swung in the acoustic coupling liquid.

2. The ultrasonic probe according to claim 1, wherein a length from said first shaft member to the coupling shaft is the same as a length from said first shaft member to said second shaft member, and a triangle formed by said first shaft member, by the coupling shaft, and by said second shaft member make up together an isosceles triangle.

3. The ultrasonic probe according to claim 1, wherein a length from said first shaft member to the coupling shaft is designed to be longer than a length from said first shaft member to the said second shaft member.

4. The ultrasonic probe according to claim 1, wherein said ultrasonic element is rotatably mounted on said second arm, a groove type rail is provided on the cubicle so that a guiding shaft disposed on the ultrasonic element is engaged with said groove type rail.

5. The ultrasonic probe according to claim 4, wherein a bearing or a resin material having low friction resistance is provided on a forward end where said groove type rail or said convex type rail comes into contact with said guiding shaft.

6. The ultrasonic probe according to claim 4, wherein an elastic material such as rubber or resin is provided on both or one of said groove type rail or said convex type rail and said guiding shaft on a portion where said groove type rail or said convex type rail and said guiding shaft come into contact with each other.

7. The ultrasonic probe according to claim 1, wherein said ultrasonic element is rotatably mounted on said second arm, a convex type rail is disposed on the cubicle, and said convex type rail is squeezed by two or more guiding shafts provided on said ultrasonic element.

8. The ultrasonic probe according to claim 7, wherein a bearing or a resin material having low friction resistance is provided on a forward end where said convex type rail comes into contact with said guiding shaft.

9. The ultrasonic probe according to claim 7, wherein an elastic material such as rubber or resin is provided on both or one of said convex type rail and said guiding shaft on a portion where said convex type rail and said guiding shaft come into contact with each other.

10. The ultrasonic probe according to claim 1, wherein said ultrasonic element is rotatably mounted with respect to said second arm, a groove type rail is provided on the cubicle, and a guiding shaft disposed on said ultrasonic element and a second guiding shaft disposed in such manner that said second guiding shaft is repelled to said guiding shaft by force of a spring are engaged on said groove type rail mounted on said frame or said ultrasonic window.

11. The ultrasonic probe according to claim 10, wherein a bearing or a resin material having low friction resistance is provided on a forward end where said groove type rail comes into contact with said guiding shaft.

12. The ultrasonic probe according to claim 10, wherein an elastic material such as rubber or resin is provided on both or one of said groove type rail and said guiding shaft on a portion where said groove type rail and said guiding shaft come into contact with each other.

13. The ultrasonic probe according to claim 1, wherein said ultrasonic element is rotatably mounted on said second arm, a convex type rail is disposed on the cubicle, and a guiding shaft provided on said ultrasonic element and a second guiding shaft provided to pull each other by force of a spring to said guiding shaft so that said convex type rail disposed on said frame or on said ultrasonic window is squeezed.

14. The ultrasonic probe according to claim 13, wherein a bearing or a resin material having low friction resistance is provided on a forward end where said convex type rail comes into contact with said guiding shaft.

15. The ultrasonic probe according to claim 13, wherein an elastic material such as rubber or resin is provided on both or one of said convex type rail and said guiding shaft on a portion where said convex type rail and said guiding shaft come into contact with each other.

16. The ultrasonic probe according to claim 1, wherein said ultrasonic element is an electronic scanning type element and is mechanically swung in a direction to perpendicularly cross the electronic scanning by said swinging mechanism.

17. The ultrasonic probe according to claim 1, wherein a length from an end portion of said second arm where said ultrasonic element is mounted to said coupling shaft is designed to be longer than a length from said first shaft member to the coupling shaft, and is designed to be longer than a length from said first shaft member to said second shaft member.

18. The ultrasonic probe according to claim 1, wherein the first shaft member is connected to a motor.

19. The ultrasonic probe according to claim 1, wherein the second shaft member is connected to the cubicle.

20. An ultrasonic probe, comprising
a cubicle,
a swinging mechanism disposed in the cubicle,
an acoustic coupling liquid sealed in the cubicle,
wherein the swinging mechanism comprising:
a first arm with one end fixed on a first shaft member,
a second arm with one end rotatably connected to the other end of said first arm via a coupling shaft,
an ultrasonic element to mutually convert electric signals and ultrasonic signals provided on the other end of the second arm,
wherein said second arm is slidably engaged with a slide bearing unit which is connected to a second shaft member, and said ultrasonic element is swung in the acoustic coupling liquid.

21. The ultrasonic probe according to claim 20, wherein said ultrasonic element is rotatably mounted on said second arm, a groove type rail is provided on the cubicle so that a guiding shaft disposed on the ultrasonic element is engaged with said groove type rail.

22. The ultrasonic probe according to claim 21, wherein a bearing or a resin material having low friction resistance is provided on a forward end where said groove type rail or said convex type rail comes into contact with said guiding shaft.

23. The ultrasonic probe according to claim 21, wherein an elastic material such as rubber or resin is provided on both or one of said groove type rail or said convex type rail and said guiding shaft on a portion where said groove type rail or said convex type rail and said guiding shaft come into contact with each other.

24. The ultrasonic probe according to claim 20, wherein said ultrasonic element is rotatably mounted on said second arm, a convex type rail is disposed on the cubicle, and said convex type rail is squeezed by two or more guiding shafts provided on said ultrasonic element.

25. The ultrasonic probe according to claim 24, wherein a bearing or a resin material having low friction resistance is provided on a forward end where said convex type rail comes into contact with said guiding shaft.

26. The ultrasonic probe according to claim 24, wherein an elastic material such as rubber or resin is provided on both or one of said convex type rail and said guiding shaft on a portion where said convex type rail and said guiding shaft come into contact with each other.

27. The ultrasonic probe according to claim 20, wherein said ultrasonic element is rotatably mounted with respect to said second arm, a groove type rail is provided on the cubicle, and a guiding shaft disposed on said ultrasonic element and a second guiding shaft disposed in such manner that said second guiding shaft is repelled to said guiding shaft by force of a spring are engaged on said groove type rail mounted on said frame or said ultrasonic window.

28. The ultrasonic probe according to claim 27, wherein a bearing or a resin material having low friction resistance is provided on a forward end where said groove type rail comes into contact with said guiding shaft.

29. The ultrasonic probe according to claim 27, wherein an elastic material such as rubber or resin is provided on both or one of said groove type rail and said guiding shaft on a portion where said groove type rail and said guiding shaft come into contact with each other.

30. The ultrasonic probe according to claim 20, wherein said ultrasonic element is rotatably mounted on said second arm, a convex type rail is disposed on the cubicle, and a guiding shaft provided on said ultrasonic element and a second guiding shaft provided to pull each other by force of a spring to said guiding shaft so that said convex type rail disposed on said frame or on said ultrasonic window is squeezed.

31. The ultrasonic probe according to claim 30, wherein a bearing or a resin material having low friction resistance is provided on a forward end where said convex type rail comes into contact with said guiding shaft.

32. The ultrasonic probe according to claim 30, wherein an elastic material such as rubber or resin is provided on both or one of said convex type rail and said guiding shaft on a portion where said convex type rail and said guiding shaft come into contact with each other.

33. The ultrasonic probe according to claim 20, wherein said ultrasonic element is an electronic scanning type element and is mechanically swung in a direction to perpendicularly cross the electronic scanning by said swinging mechanism.

34. The ultrasonic probe according to claim 20, wherein the first shaft member is connected to a motor.

35. The ultrasonic probe according to claim 20, wherein the second shaft member is connected to the cubicle.

* * * * *